United States Patent
Jin et al.

(10) Patent No.: US 11,105,766 B2
(45) Date of Patent: Aug. 31, 2021

(54) METHODS AND SYSTEMS FOR REAL-TIME MONITORING OF IN SITU BIOACTIVITY AND BIODEGRADATION

(71) Applicant: Advanced Environmental Technologies LLC, Fort Collins, CO (US)

(72) Inventors: Kylan Jin, Fort Collins, CO (US); Paul Fallgren, Fort Collins, CO (US); Song Jin, Fort Collins, CO (US); Nicholas Santiago, Colorado Springs, CO (US)

(73) Assignee: Advanced Environmental Technologies, LLC, Fort Collins, CO (US)

( * ) Notice: Subject to any disclaimer, the term of this patent is extended or adjusted under 35 U.S.C. 154(b) by 189 days.

(21) Appl. No.: 16/285,030

(22) Filed: Feb. 25, 2019

(65) Prior Publication Data
US 2020/0271616 A1    Aug. 27, 2020

(51) Int. Cl.
| | |
|---|---|
| *G01N 27/327* | (2006.01) |
| *G01N 27/28* | (2006.01) |
| *G01N 33/24* | (2006.01) |
| *G01N 33/18* | (2006.01) |

(52) U.S. Cl.
CPC ....... *G01N 27/3277* (2013.01); *G01N 27/286* (2013.01); *G01N 33/1826* (2013.01); *G01N 33/24* (2013.01); *G01N 2033/243* (2013.01)

(58) Field of Classification Search
None
See application file for complete search history.

(56) References Cited

U.S. PATENT DOCUMENTS

| | | | |
|---|---|---|---|
| 7,858,243 B2 | 12/2010 | Jin et al. | |
| 9,045,354 B2 | 6/2015 | Jin et al. | |
| 2015/0353386 A1 | 12/2015 | Jin et al. | |
| 2016/0230206 A1* | 8/2016 | Lovley | ............. C12Q 1/02 |
| 2018/0319666 A1 | 11/2018 | Jin et al. | |

FOREIGN PATENT DOCUMENTS

| | | | |
|---|---|---|---|
| CN | 103645231 A | * | 3/2014 |
| CN | 211148508 U | | 7/2020 |

OTHER PUBLICATIONS

Williams, et al. "Electrode-Based Approach for Monitoring In Situ Microbial Activity During Subsurface Bioremediation", Environmental Science & Technology, 44(1), p. 47-54, Jan. (Year: 2010).*

(Continued)

*Primary Examiner* — J. Christopher Ball
(74) *Attorney, Agent, or Firm* — Santangelo Law Offices, P.C.

(57) ABSTRACT

Embodiments of the present invention provide a portable bioelectrochemical electrical signal measuring device that may have at least one anode, at least one cathode, an anode-cathode connector between said at least one anode and said at least one cathode, a load connector between a load and said at least one anode and at least one cathode, and a data meter connected to said load connector wherein the device may measure an electrical signal of a matrix to perhaps determine the microbial activity in the matrix.

22 Claims, 13 Drawing Sheets

(56) References Cited

OTHER PUBLICATIONS

C. Wardman, et al., "Real-time monitoring of subsurface microbial metabolism with graphite electrodes", Frontiers in Microbiology, 5, Article #621, pp. 1-7, Nov. (Year: 2014).*

L. Peixoto, et al. "In situ microbial fuel cell-based biosensor for organic carbon", Bioelectrochemistry, 81(2):p. 99-103, Jun. (Year: 2011).*

Buchmann, N. 2000. Biotic and abiotic factors controlling respiration rates in Picea abies stands. Soil Biol. Biochem. 32:1625-1635.

Chen, Z., Niu, Y., Zhao, S., Khan, A., Ling, Z., Chen, Y., Liu, P., Li, X. 2016. A novel biosensor for p-nitrophenol based on a an aerobic anode microbial fuel cell. Biosensors Bioelectronics 85:860-868.

Cook, F.J., Orchard, V.A. 2008. Relationships between soil respiration and soil moisture. Soil Biol. Biochem. 40:1013-1018.

Dumas, C., Monica, A., Feron, D., Basseguy, R., Etcheverry, L., Bergel, A. 2007. Marine microbial fuel cell: Use of stainless steel electrodes as anode and cathode materials. Electrochim. Acta 53:468-473.

Dunaj, S.J., Vallino, J.J., Hines, M.E., Gay, M., Kobyljanec, C., Rooney-Varga, J.N. 2012. Relationships between soil organic matter, nutrients, bacterial community structure, and the performance of microbial fuel cells. Environ. Sci. Technol. 46:1914-1922.

Fallgren, P.H., Jin, S., Zhang, R., Stahl, P.D. 2010. Empirical models estimating carbon dioxide accumulation in two petroleum hydrocarbon-contaminated soils. Biorem. J. 14:98-108.

Huang, D.-Y., Zhou, S.-G., Chen, Q., Zhao, B., Yuan, Y., Zhuang, L. 2011. Enhanced anaerobic degradation of organic pollutants in a soil microbial fuel cell. Chem. Eng. J. 172:647-653.

Huggins, T., Fallgren, P.H., Jin, S., Ren, Z.J. 2013. Energy and performance comparison of microbial fuel cell and conventional aeration treating of wastewater. J. Microb. Biochem. Technol. S6:002.

Jiang, Y.-B., Zhong, W.-H., Han, C., Deng, H. 2016. Characterization of electricity generated by soil in microbial fuel cells and the isolation of soil source exoelectrogenic bacteria. Front. Microbiol. 7:1776.

Jin, S., Fallgren, P.H. 2014. Feasibility of using bioelectrochemical systems for bioremediation. In S. Das (ed.) Microbial Biodegradation and Bioremediation. Elsevier, London, pp. 389-405.

Li, W.-W., Yu, H.-Q., He, Z. 2014. Towards sustainable wastewater treatment by using microbial fuel cells-centered technologies. Energy Environ. Sci. 7:911-924.

Logan B.E. Regan, J.M. 2006. Microbial fuel cells—challenges and applications. Environ. Sci. Technol. 40:5172-5180.

Lu, L., Huggins, T., Jin, S., Zuo, Y., Ren, Z.J. 2014a. Microbial metabolism and community structure in response to bioelectrochemically enhanced remediation of petroleum hydrocarbon-contaminated soil. Environ. Sci. Technol. 48:4021-4029.

Lu, L. Yazdi, H. Jin, S. Zuo, Y. Fallgren, P.H. Ren, Z.J. 2014b. Enhanced bioremediation of hydrocarbon-contaminated soil using pilot-scale bioelectrochemical systems. J. Hazard. Mater. 274:8-15.

Peixoto, L., Min, B., Martins, G., Brito, A.G., Kroff, P., Parpot, P., Angelidaki, I., Nogueira, R. 2011. In situ microbial fuel cell-based biosensor for organic carbon. Bioelectrochem. 81:99-103.

Scott, K., Cotlarciuc, I., Head, I., Katuri, K.P., Hall, D., Lakeman, J.B., Browning, D. 2008. Fuel cell power generation from marine sediments: Investigation of cathode materials. J. Chem. Technol. Biotechnol. 83:1244-1254.

Vicari, F., D'Angelo, A., Galia, A., Quatrini, P., Scialdone, O. 2016. A single-chamber membraneless microbial fuel cell exposed to air using Shewanella putrefaciens. J. Electroanalytical Chem. 783:268-273.

Wester, K., Sudirjo, E., Buisman, C.J.N., Strik, D.P.B.T.B. 2015. Electricity generation by a plant microbial fuel cell with an integrated oxygen reducing biocathode. Appl. Energy 137:151-157.

Yuan, Y., Zhou, S., Zhuang, L. 2010. A new approach to in situ sediment remediation based on air-cathode microbial fuel cells. J. Soils Sed. 10:1427-1433.

Ringeisen, B.R., Ray, R., Little, B. 2007. A miniature microbial fuel cell operating with an aerobic anode chamber. J. Power Sources 165:591-597.

Logan, B. E. et. al., Microbial Fuel Cells: Methodology and Technology. Critical Review. vol. 40, No. 17. 2006. Environmental Science and Technology. 5181-5192.

* cited by examiner

METHODS AND SYSTEMS FOR REAL-TIME MONITORING OF IN SITU BIOACTIVITY AND BIODEGRADATION

FIELD OF THE INVENTION

Embodiments of the present invention relate to portable bio-electro-chemical systems. More specifically, the present invention may relate to the design, construction, and utilization of portable bioelectrochemical systems or devices perhaps to monitor microbial activity, biodegradation, biotransformation, concentrations of organic/inorganic chemicals, under in situ or ex situ conditions, or the like.

BACKGROUND OF INVENTION

Bioelectrochemical (BEC) systems are technologies that can enhance and/or exploit microbial oxidation-reduction (redox) activities. Some BEC technologies can generate electrical potential by providing an alternative electron acceptor for microbial respiration. In BEC systems, organic compounds can be biodegraded, which may release electrons that can be transferred to a solid electrode (e.g., an anode or the like). The electrons may move through a load to that may generate an electrical potential, and then oxygen ($O_2$) may be reduced to water at a cathode. In the past, this process has been studied with the conversion of wastewater compounds to energy in the form of microbial fuel cells, while others may have focused on enhancing contaminant biodegradation. There may be different configurations for BEC biodegradation systems such as open-type systems which may be applied in soils and sediments. Studies have demonstrated that electrical potential can be generated from the degradation of organic compounds in soil using a BEC system, where compounds may include soil organic matter (SOM) and organic contaminants such as petroleum hydrocarbons or the like. It should be noted that despite the preferential bacterial electron transfer to $O_2$, within the rhizosphere, the conditions may be adequate for bacterial electron transfer to a BEC system anode, and bacteria may be capable of transferring electrons to a BEC system anode. This may be common in soils and can transfer electrons to a BEC system anode even in the presence of $O_2$.

The amount of electrical potential produced by a BEC system may be related to the level of microbial activity in a system, where studies have indicated that factors affecting microbial activity may be proportionally reflected in the produced electrical potentials. Therefore, an electrical potential measured from a BEC system can indicate not only the level of microbial activity, but perhaps also an amount of organic compounds, temperature, nutrient concentrations, and other parameters in a system. Since soil microbial activity (e.g., biodegradation) may be affected by the amount and quality of SOM, amount and type of nutrients, moisture, temperature, oxygen levels, salinity, and pH, a BEC system inserted in soil could indicate the level of microbial activity in the surrounding soil from the electrical potential measurements. The electrical potential measurements can correlate with other standard indicators that quantify microbial activity to indicate the microbial activity level. The measurement of microbial activity in soil may be an indicator of the level of biodegradation of organic matter or compounds, and may be important in agriculture or land management in determining overall soil health. This application could also be applicable to environmental remediation and wastewater treatment, where the level of microbial activity may be indicative of the effectiveness of a treatment in not only soils, but also in groundwater, sediments, surface water, and wastewater, energy process matrix (e.g., liquid phase in biogas process), or the like.

Environmental and energy process monitoring may be limited to analytical costs, though frequent monitoring may provide and ensure optimal operation or performance of these processes. Earlier patents, such as U.S. Pat. Nos. 9,045,354 and 7,858,243B2) provide bioelectrochemical systems (BECS) designed to enhance biological and chemical degradation and transformation of different pollutants in different environmental matrices (e.g., soil, sediments, surface and groundwater). Bioelectrochemical (BEC) technologies have been by offering a method of monitoring microbial activities simultaneously with consumption and/or transformation of organic and inorganic compounds in different matrices, saving the cost of collecting samples and analyses. Within a BEC device, electron flow can generate voltage. An amount of voltage generated in a BEC device may correlate with the amount of electron-donating compounds (including many contaminants) in a surrounding matrix; therefore, it may be possible to determine the concentrations of electron donor based on voltages generated in a BEC device.

A configuration of the BEC devices may be important, such as an open-type configuration which may allow for maximum contact with the matrix of concern. A tubular-configuration perhaps with an anode facing outward while an inner cathode may be in contact with $O_2$ (such as but not limited to via an inner tube) has been developed and demonstrated for enhancing petroleum hydrocarbon biodegradation in soils. This type of configuration may be suitable for monitoring organic compound (e.g., electron donor) consumption/biodegradation, which may correlate with the voltage profiles within the BEC device. Also, this configuration may allow such a BEC device to be portable.

For applications of monitoring reduction of electron-accepting compounds (e.g., oxyanions and chlorinated ethenes), the configurations described above may be altered by having a cathode facing outward, while an anode chamber may be a closed inner tube, perhaps containing an anode as well as microorganisms inoculated by using the indigenous soil/groundwater mixture and even standard electron donors. When microbes may degrade standard electron donors, electrons can be released through the device perhaps to be accepted by electron accepting compounds (including, but not limited to, many contaminants such as chlorinated ethenes, hexavalent chrome, nitrate, even perfluorinated compounds, or the like) in the surrounding matrix.

SUMMARY OF INVENTION

The present invention includes a variety of aspects, which may be selected in different combinations based upon the particular application or needs to be addressed. In various embodiments, the invention may include bioelectrochemical systems or devices perhaps to monitor microbial activity, biodegradation, biotransformation, concentrations of organic/inorganic chemicals, under in situ or ex situ conditions, or the like.

It is an aspect of embodiments of the present invention to provide a portable bioelectrochemical device for measuring organic and inorganic compound concentration changes in environmental and energy process matrices or the like.

It is an aspect of embodiments of the present invention to provide a portable bioelectrochemical device for measuring microbial activities in environmental and energy process matrices.

Naturally, further objects, goals, and embodiments of the inventions are disclosed throughout other areas of the specification and figures.

DETAILED DESCRIPTION OF PREFERRED EMBODIMENTS

Figure 1:
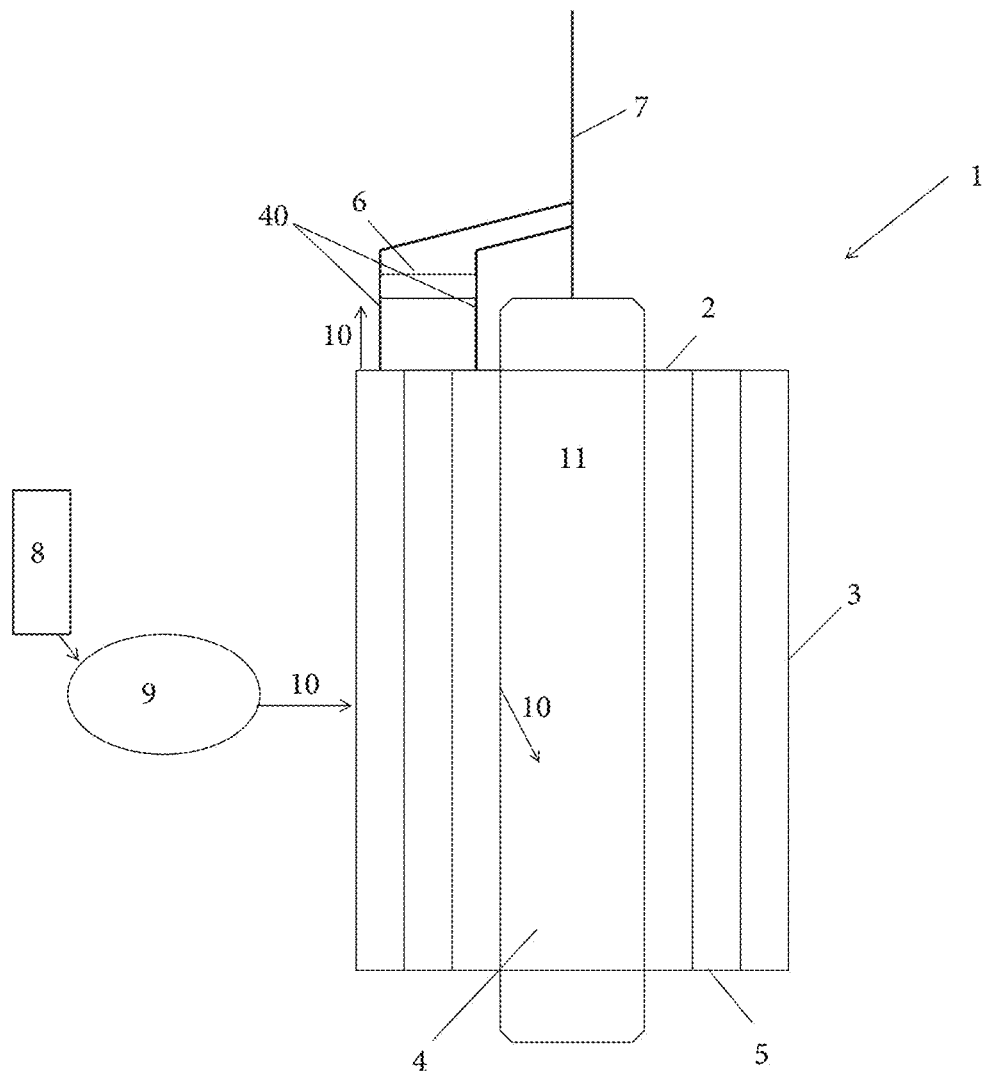
FIG. 1 shows a non-limiting example of a general design of a portable bioelectrochemical device in accordance with the various embodiments of the present invention.

As mentioned earlier, the present invention includes a variety of aspects, which may be combined in different ways. The following descriptions are provided to list elements and describe some of the embodiments of the present invention. These elements are listed with initial embodiments; however, it should be understood that they may be combined in any manner and in any number to create additional embodiments. The variously described examples and preferred embodiments should not be construed to limit the present invention to only the explicitly described systems, techniques, and applications. The specific embodiment or embodiments shown are examples only. The specification should be understood and is intended as supporting broad claims as well as each embodiment, and even claims where other embodiments may be excluded. Importantly, disclosure of merely exemplary embodiments are not meant to limit the breadth of other more encompassing claims that may be made where such may be only one of several methods or embodiments which could be employed in a broader claim or the like. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the present invention may include a microbial activity measurement system comprising a portative, transitory bioelectrochemical insert capable of measuring electrical signals originated from microbial metabolisms in a natural matrix containing microorganisms or biological enzymes; wherein said portative, transitory bioelectrochemical insert comprises: at least one anode; at least one cathode; an anode-cathode connector between said at least one anode and said at least one cathode; a load connector between a load and said anode and cathode; and perhaps even a data meter connectable to said load connector or the like. Other embodiments may provide a method of measuring microbial activity comprising the steps of providing a portable bioelectrochemical electrical signal measuring device comprising at least one anode; at least one cathode; an anode-cathode connector between said at least one anode and said at least one cathode; a load connector between a load and said anode and cathode; and a data meter connected to said load connector; providing a natural matrix containing microorganisms or biological enzymes; inserting said portable bioelectrochemical electrical signal measuring device into said natural matrix containing microorganisms or biological enzymes; measuring an electrical signal of said natural matrix with said portable bioelectrochemical electrical signal measuring device; removing said portable bioelectrochemical electrical signal measuring device from said matrix; and perhaps even determining microbial activity in said remediation matrix based on said measured electrical signal, or the like.

Figure 14:
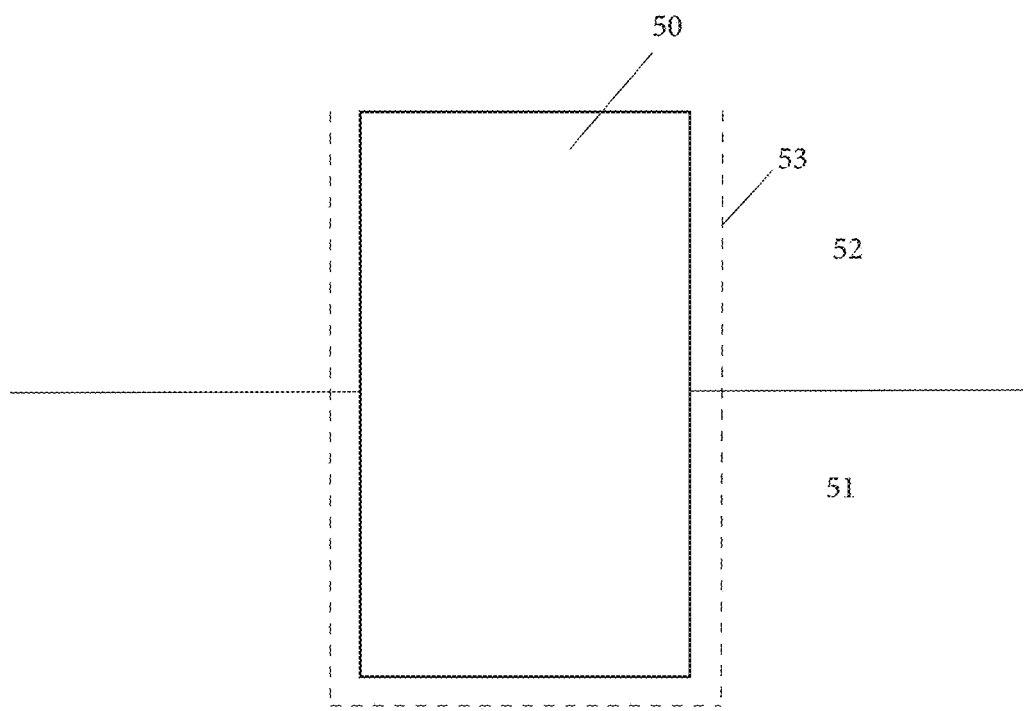
FIG. 14 shows a representation of an example of a microbial activity measurement system in accordance with the various embodiments of the present invention.

FIG. 14 shows a non-limiting example of a representation of a portable bioelectrochemical electrical signal measuring device (50), perhaps called a BioRemeter, which may be inserted into a matrix (51) perhaps with some of it exposed to air (52). In some embodiments, portable bioelectrochemical electrical signal measuring device (50) may be portative, transitory bioelectrochemical insert. A portative, transitory bioelectrochemical insert may be capable of measuring electrical signals perhaps originated from microbial metabolisms such as in a natural matrix containing microorganisms or biological enzymes. Biological enzymes may be any kinds of enzyme that may be produced by a microorganism. Electrical signals may include, but is not limited to, voltage and amperage. Such device may portable so that a user may be able to easily carry perhaps even by hand a device to take measurement of a matrix. A transitory device may be temporarily used in that it may not be permanently installed into a matrix.

Embodiments of the present invention may provide a system where at least part of a cathode may be exposed to air (52) when a device may be inserted in a matrix. An anode may be placed in a matrix so that it may be substantially surrounded by a matrix when inserted.

A matrix (51) may be a natural matrix which may be naturally existing environments such as, but not limited to, soils, surface water, groundwater and sediments, perhaps all containing microbes and therefore microbial metabolisms. A natural matrix may include cultivating land and contaminants that are made or perhaps even contributed by humans. A matrix may include microorganisms and/or biological enzymes and may be an environment with at least one originally contained organic compound, naturally occurring organic compound, contaminant, anthropogenic contaminant, or the like. Compounds and contaminants may include, but are not limited to, compounds containing carbon, soil organic matter, fats, carbohydrates, proteins, organic acids, benzene, toluene, ethyl benzene, xylenes, general petroleum hydrocarbons, other organic compounds, any combination thereof, or the like. A matrix may be an area within and perhaps even surrounding an environment that is undergoing remediation, such as a remediation matrix. Examples of a matrix include, but are not limited to, soil, groundwater, sediment, surface water, wastewater, energy process matrix, a liquid phase in biogas process, or the like.

Measured electrical signals (55) may be correlated (56) to microbial activity in a matrix which may provide a determination of the microbial activity in a matrix. In some embodiments, a matrix may be a wastewater treatment and a system may measure microbial activity perhaps correlated to real-time monitoring a chemical oxygen demand of wastewater treatment. In another embodiments, a matrix may be soil and a system may measure microbial activity perhaps correlated to real-time monitoring of carbon dioxide of the soil. In yet another embodiment, a matrix may be contaminated groundwater and a system may measure microbial activity perhaps correlated to real-time monitoring of a voltage in the contaminated groundwater. In some embodiments, a matrix may include microbial enhancement of fuel and a system may measure microbial activity perhaps correlated to real-time monitoring of benzene in the fuel.

Embodiments of the present invention may include a portable bioelectrochemical device perhaps for monitoring organic and inorganic compound concentration changes and microbial activity in environmental and energy processes, which may include, but are not limited to, municipal wastewater treatment, industrial wastewater treatment, in situ and ex situ environmental remediation, soil treatment, groundwater treatment, surface water treatment, anaerobic digestion, bioenergy processes, coal biogasification, landfill leachate treatment, or the like. The voltage generated from the portable bioelectrochemical device may be correlated with organic and inorganic compound changes and microbial activity. Microbial activity measurement systems may be applicable to agriculture, land management, land restoration, environmental remediation, wastewater treatment, energy production (e.g., biogas), or the like. There may be a number of different configurations that may be specific to an application, where some examples are described herein; however these examples are not limited to the designs included but can be modified as needed.

FIG. 1 shows a non-limiting example of a microbial activity measurement system (1) that in some embodiments may include at least one cathode (2), at least one anode (3), a hollow tube (4), a separator (5), a load (6), a load connector (40) which may be between a load and an anode and cathode, a line (7) to a surface, an organic electron donor (8), bacteria (9), movement of electrons (10), and perhaps even oxygen (11), any combination thereof, or the like. As can be understood from FIG. 1, a single portable bioelectrochemical device may be used to monitor changes in concentrations and or general quantities of electron-donating compounds and microbial activities.

A matrix may have electron-donating compounds which may include, but are not limited to, organic acids, volatile fatty acids, polylactate, polysaccharides, oils, emulsified oils, sugars, cellulose, starch, molasses, petroleum hydrocarbons, volatile organic compounds, semi-volatile organic compounds, ethers, fuel oxygenates, ketones, alcohols, amines, amides, monoaromatic compounds, sulfide, iron, urea, ammonia, natural organic matter, organic matter, chemical oxygen demand, biological oxygen demand, or the like. In some embodiments, a perforated casing (53) perhaps located around a portable bioelectrochemical device may expose an anode to a surrounding matrix (51). Each portable bioelectrochemical device may include at least one anode and at least one cathode. Some embodiments may include a hollow tube (4) which may be a perforated tube, a sealed hollow tube, a hollow tube separator, or the like. For example, in some embodiments, a hollow tube may separate at least one cathode from at least one anode. An anode and/or a cathode may surround a sealed hollow tube or pipe, or the like. An anode may be fixed as an outer layer, perhaps even an outmost layer, surrounding a hollow tube or pipe or the like. A cathode may be fixed as an inner layer, perhaps as an innermost layer, surrounding and may even be directly in contact with a hollow tube or pipe or the like. A hollow tube or pipe or the like may be perforated perhaps to allow contact with air or oxygen or the like. A hollow tube maybe filled with air, a solid, a liquid, dissolved oxygen, oxygen releasing compounds, any combination thereof, or the like. Oxygen releasing compounds may include, but are not limited to, magnesium peroxide, calcium peroxide, hydrogen peroxide, percarbonate, ozone, organic peroxides, permanganate, persulfate, ferrate, or the like. Possible hollow tube or pipe materials may include, but are not limited to, plastic, polyvinyl chloride, polymethyl methacrylate, fiberglass, high-density polytetrafluoroethylene, other plastics, or the like. Possible anode materials may include, but are not limited to, carbonaceous materials, man-made carbonaceous materials, naturally existing carbonaceous materials, granulated activated carbon, biochar, carbon nanotubes, graphite, graphene, reduced-graphene oxide, other graphene-based materials, coal, petroleum coke, anthracite, carbon clothe, carbon fiber, carbon fiber brush, any combination thereof, or the like. Possible cathode materials may include, but are not limited to, fine stainless steel mesh, stainless steel foam, iron filings, stainless steel rod, mesh, stainless steel wool, stainless steel foam, stainless steel brush, carbon cloth, activated carbon, carbon paper, or the like. An electrode such as the cathode or anode may or may not be coated with a catalyst, which may include, but is not limited to, platinum/carbon (Pt/C) catalyst, iridium catalyst, zinc oxide, lead oxides, titanium oxides (rutile), or the like. In some embodiments, at least part of a cathode may be coated with a waterproof but air permeable material, which may include, but is not limited to, polytetrafluoroethylene, poly(dimethylsiloxane), or the like. In embodiments, one side of a cathode may be coated with a material. An anode and cathode may be connected by a load connector (40) which may include respective leads or even receptacles, and may even be a wire connector which may connect a load or even a resistor such as a simple resistor to anodes and cathodes.

Figure 2:
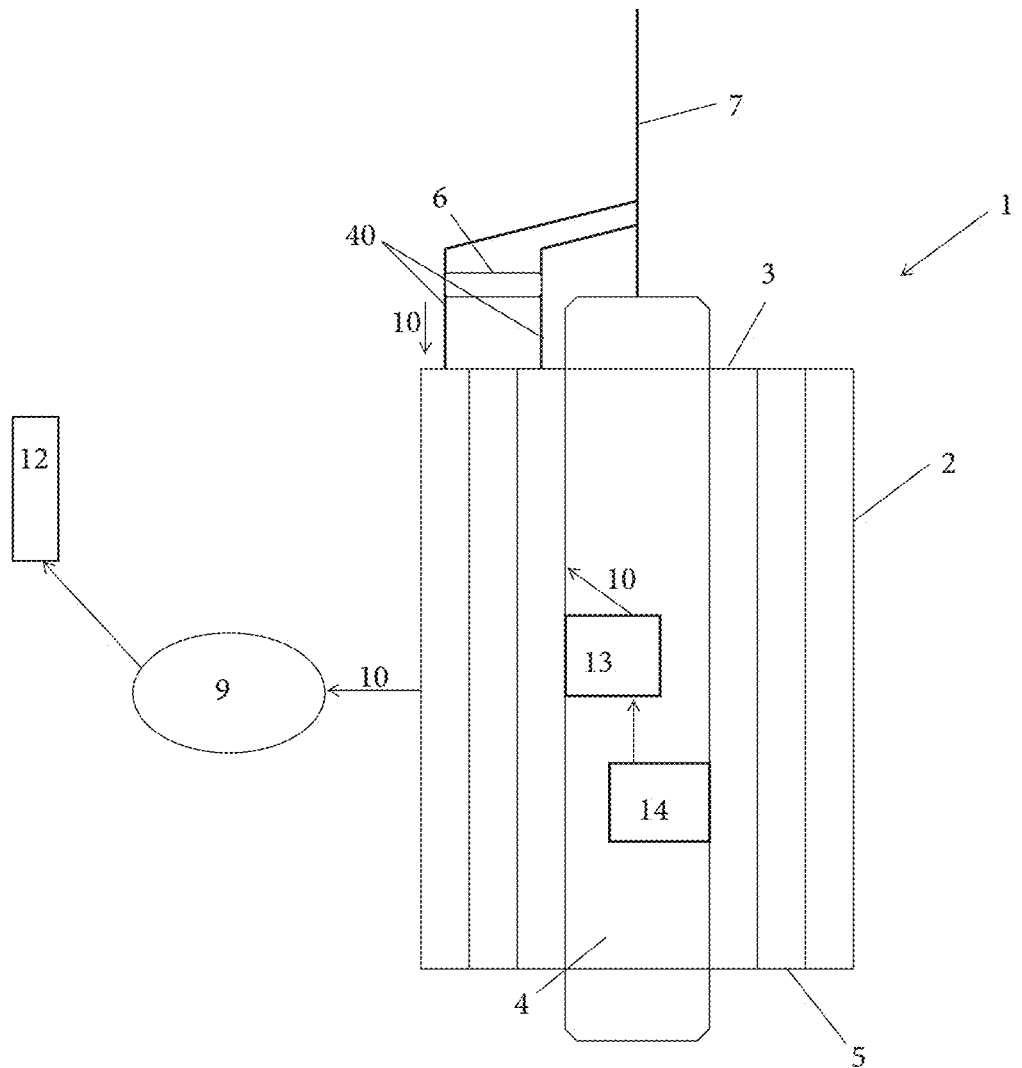
FIG. 2 shows a non-limiting example of general design of a portable bioelectrochemical device in accordance with the various embodiments of the present invention.

FIG. 2 shows an example of a microbial activity measurement system (1) that in some embodiments may provide a cathode (2), an anode (3), a sealed tube (4), a separator (5), a load (6), a line (7) to a surface, an electron acceptor (12), bacteria (9), movement of electrons (10), bacteria (13), and an electron donor (14). As can be understood from FIG. 2, a single portable bioelectrochemical device may monitor electron-accepting compound changes and perhaps even microbial activity in a matrix. Electron-accepting compounds may include, but are not limited to, oxyanions, chlorinated solvents, halogenated hydrocarbons, dioxins, polychlorinated biphenyls, chlorobenzenes, phenols, chlorophenols, perfluorinated compounds, chemical oxygen demand, heavy metals, hexavalent chromium, arsenic, selenium, nitrate, perchlorate, carbon dioxide, sulfur oxides, nitrogen oxides or the like. A perforated casing perhaps around a portable bioelectrochemical device may expose a cathode to the surrounding matrix. Each portable bioelectrochemical device may include at least one cathode and at least one anode, perhaps each surrounding a sealed hollow tube or pipe, or the like. A cathode may be fixed as the outer layer, or even an outermost layer, surrounding a hollow tube or pipe or the like. An anode may be fixed as an inner layer, perhaps as an innermost layer, surrounding and even directly in contact with a hollow tube or pipe or the like. A hollow tube or pipe may be perforated perhaps to allow contact with microorganisms or enzymes. A hollow tube maybe filled with a solution of electron-donating compounds and perhaps even microorganisms.

In some embodiments, electron-donating compounds may include, but are not limited to, volatile fatty acids, sugars, oils, molasses, alcohols, or the like. Microorganisms may include, but are not limited to indigenous, indigenous matrix or even commercially available strains, microorganisms that are capable of degrading the contained electron-donating compounds, they may consist of, but are not limited to, facultative bacteria, iron-reducing bacteria, sulfate-reducing bacteria, metal-reducing bacteria, denitrifying bacteria, methane-producing bacteria, archaea, dechlorinating bacteria, fermentative bacteria, or the like. Possible hollow tube or pipe materials include, but are not limited to, polyvinyl chloride, polymethyl methacrylate, fiberglass, high-density polytetrafluoroethylene, other plastics, or the like. Possible anode materials may include, but are not limited to, carbonaceous materials (man-made or naturally existing), granulated activated carbon, biochar, graphite, coal, petroleum coke, anthracite, carbon clothe, carbon fiber, carbon fiber brush, any combination thereof, or the like. Possible cathode materials may include, but are not limited to, fine stainless steel mesh, stainless steel foam, iron filings, stainless steel rod, mesh, stainless steel wool, stainless steel foam, and stainless steel brush, carbon cloth, activated carbon, carbon paper, or the like. The cathode may or may not be coated with a catalyst, which may include, but is not limited to, platinum/carbon (Pt/C) catalyst, iridium catalyst, zinc oxide, lead oxides, titanium oxides (rutile), or the like. On one side, a cathode may be coated with a waterproof but air permeable material, which may include, but is not limited to, polytetrafluoroethylene or poly(dimethylsiloxane). An anode and cathode may be connected to respective leads or even receptacles, where wire connectors may connect a load or even a simple resistor to anodes and cathodes.

Figure 3:
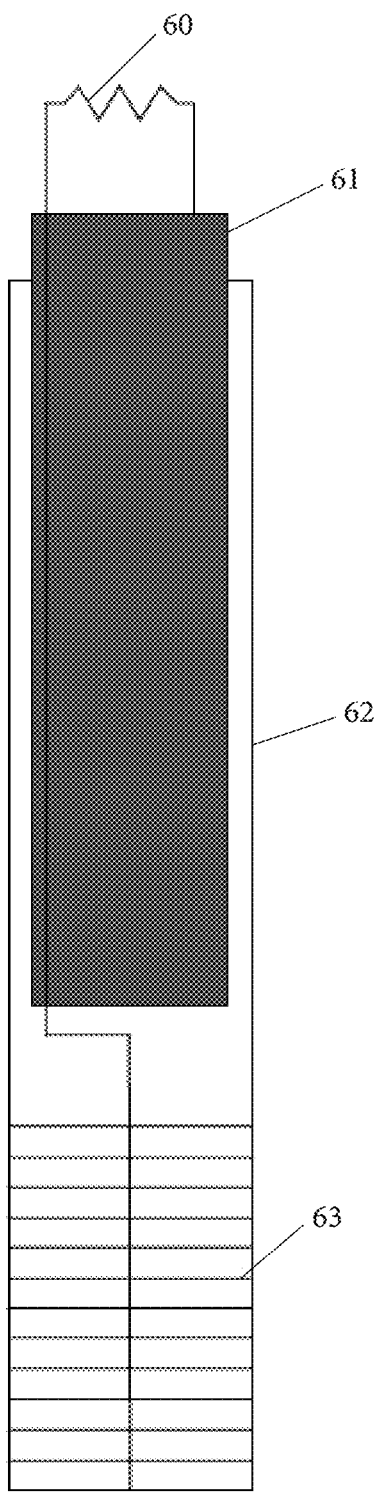
FIG. 3 shows a non-limiting example of a general design of a portable bioelectrochemical device in accordance with the various embodiments of the present invention.
Figure 4:
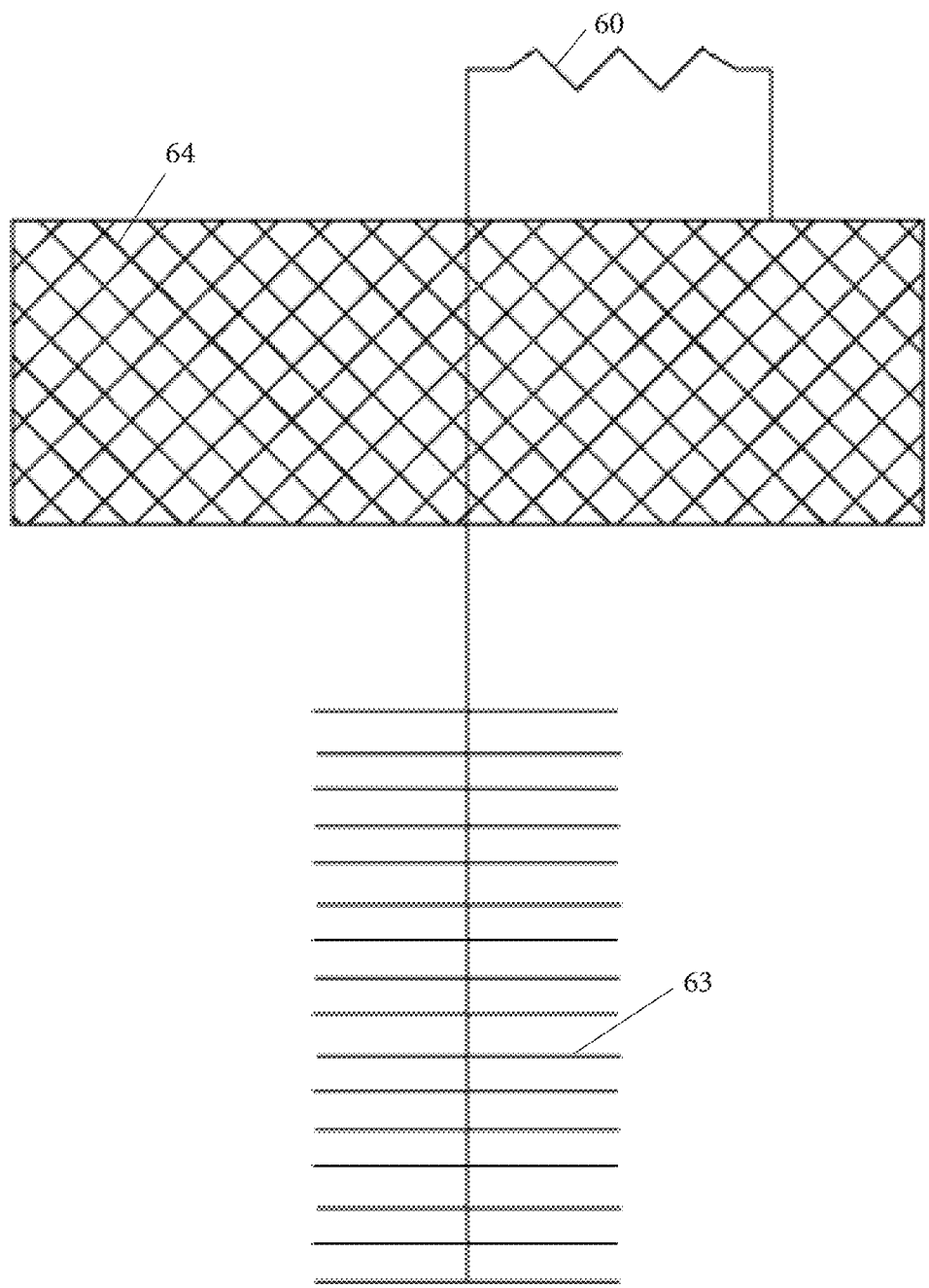
FIG. 4 shows a non-limiting example of a general design of a portable bioelectrochemical device in accordance with the various embodiments of the present invention.
Figure 5:
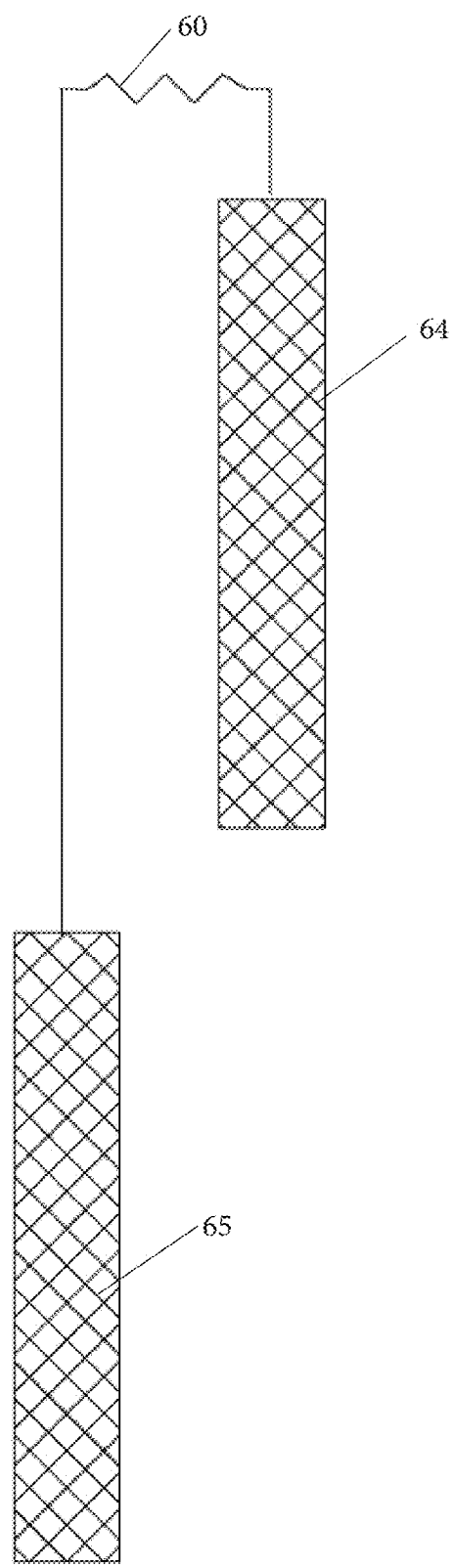
FIG. 5 shows a non-limiting example of a general design of a portable bioelectrochemical device in accordance with the various embodiments of the present invention.
Figure 6:
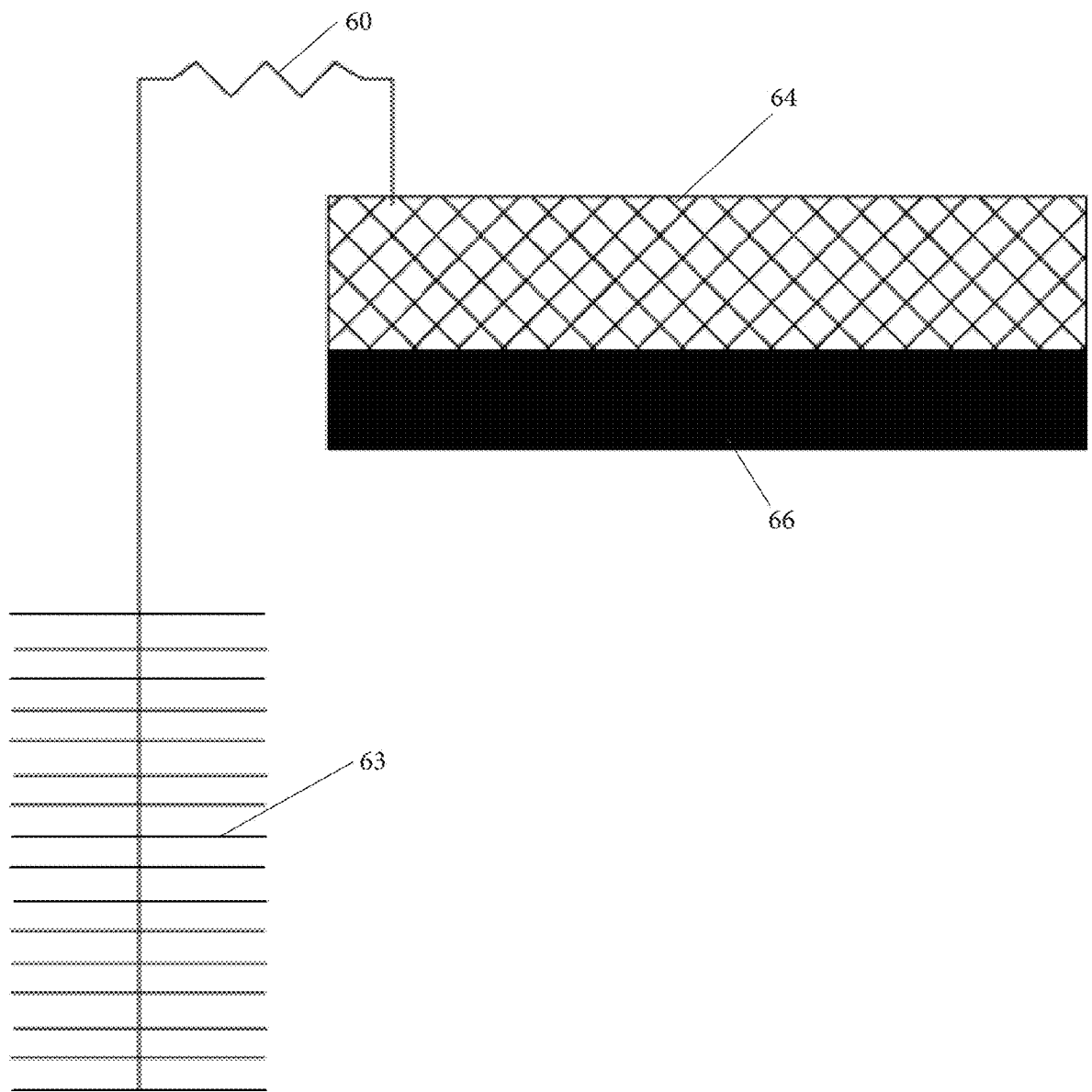
FIG. 6 shows a non-limiting example of a general design of a portable bioelectrochemical device in accordance with the various embodiments of the present invention.
Figure 7:
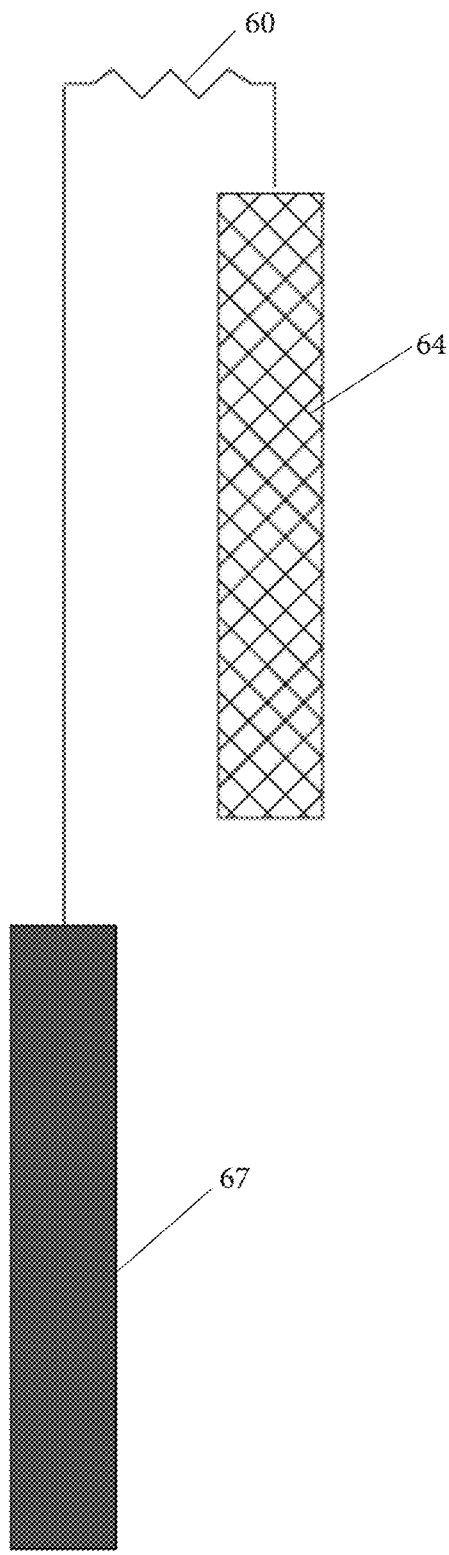
FIG. 7 shows a non-limiting example of a general design of a portable bioelectrochemical device in accordance with the various embodiments of the present invention.

FIGS. 3, 4, 5, 6, and 7 are examples of alternative configurations for a portable bioelectrochemical device that may monitor the changes in concentrations and or general quantities of electron-donating compounds and microbial activities. FIG. 3 shows a non-limiting example of a general design of a portable bioelectrochemical device in accordance with the various embodiments of the present invention, which may provide a load (60), a carbon fabric cathode (61), an outer casing (e.g., PVC) (62), and a stainless-steel bristled anode (63). FIG. 4 shows a non-limiting example of a general design of a portable bioelectrochemical device in accordance with the various embodiments of the present invention, which may provide a load (60), a stainless-steel bristled anode (63), and a stainless-steel mesh cathode (64). FIG. 5 shows a non-limiting example of a general design of a portable bioelectrochemical device in accordance with the various embodiments of the present invention, which may provide a load (60), a stainless-steel mesh cathode (64), and a stainless-steel mesh anode (65). FIG. 6 shows a non-limiting example of a general design of a portable bioelectrochemical device in accordance with the various embodiments of the present invention, which may provide a load (60), a stainless-steel bristled anode (63), and a stainless-steel mesh cathode (64) with catalyst coating (66) which can include any catalyst and mixture as indicated herein. FIG. 7 shows a non-limiting example of a general design of a portable bioelectrochemical device in accordance with the various embodiments of the present invention, which may provide a load (60), a stainless-steel mesh cathode (64), and a carbon fabric anode (67).

Electron-donating compounds may include, but are not limited to, organic acids, volatile fatty acids, polylactate, polysaccharides, emulsified oils, sugars, molasses, petroleum hydrocarbons, volatile organic compounds, semi-volatile organic compounds, ethers, fuel oxygenates, ketones, alcohols, amines, amides, monoaromatic compounds, sulfide, iron, urea, ammonia, chemical oxygen demand, biological oxygen demand, or the like. Each portable bioelectrochemical device may include at least one anode and at least one cathode, perhaps each surrounding a sealed hollow tube or pipe, or the like. Possible anode materials may include, but are not limited to, stainless steel, stainless steel brush, stainless steel mesh, other metals, metal minerals, carbonaceous materials (man-made or naturally existing), granulated activated carbon, biochar, graphite, coal, petroleum coke, anthracite, carbon clothe, carbon fiber, carbon fiber brush, any combination thereof, or the like. Possible cathode materials may include, but are not limited to, fine stainless steel mesh, stainless steel foam, iron filings, stainless steel rod, mesh, stainless steel wool, stainless steel foam, and stainless steel brush, carbon cloth, activated carbon, carbon paper, or the like. The cathode may or may not be coated with a catalyst, which may include, but is not limited to, platinum/carbon (Pt/C) catalyst, iridium catalyst, zinc oxide, lead oxides, titanium oxides (rutile), or the like. An anode and cathode may be connected to respective leads or even receptacles, where wire connectors may connect a load or even a simple resistor to anodes and cathodes.

The present invention may be connected to each side of the load to other devices perhaps for voltage data acquisition or data recovery systems may be connected as the load.

Figure 8:
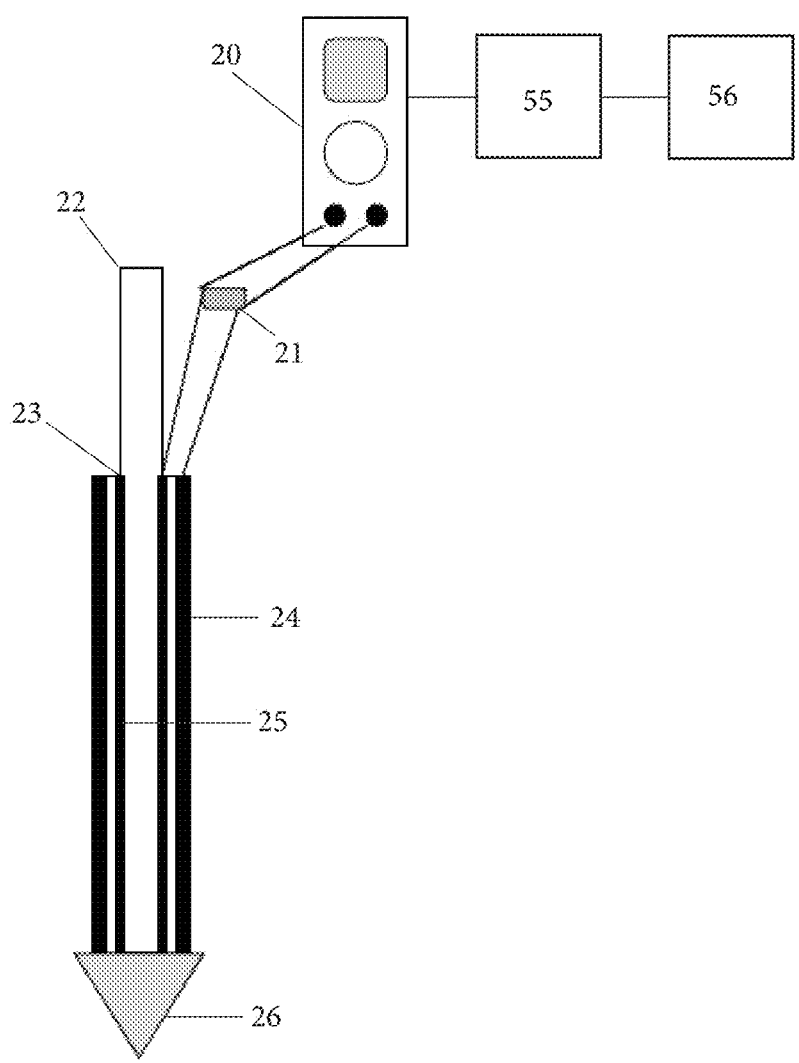
FIG. 8 shows a non-limiting example of a portable hollow tubular BES in accordance with the various embodiments of the present invention.
Figure 9:
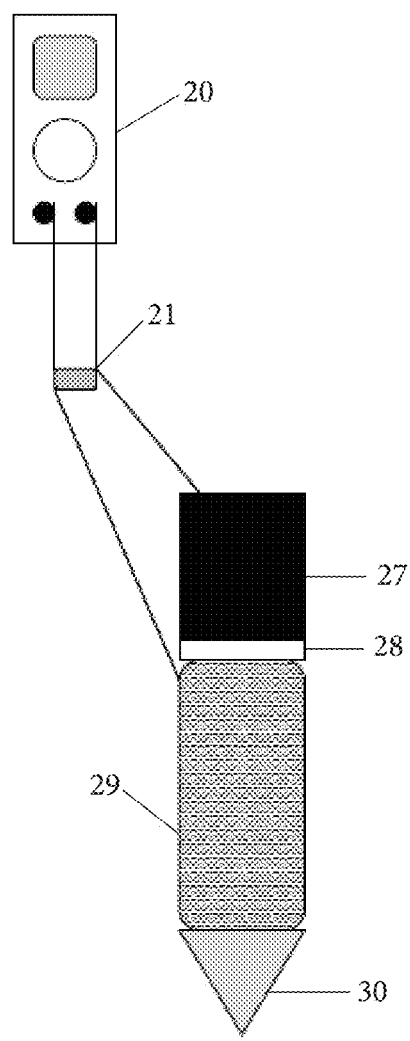
FIG. 9 shows a non-limiting example of and an open two-sectioned BES in accordance with the various embodiments of the present invention.

FIGS. 8 and 9 shows two non-limiting example designs for use of a device. FIG. 8 provides a non-limiting example of tubular-type BEC system where an anode may be in contact with soil and a cathode may be in direct contact with a center-perforated tube perhaps to react with $O_2$ in ambient air. FIG. 8 includes a data meter (20), a load (21), a center hollow tube (22), a separator (23) such as, but not limited to a middle wrapped layer, an anode (24) such as, but not limited to an outer wrapped layer, a cathode (25) such as, but not limited to an inner wrapped layer, and perhaps even a spike (26). A data meter (20) may be connectable to a load connector, and may include, but is not limited to a multimeter, voltmeter, electrical data logger, or the like.

FIG. 9 provides an alternative non-limiting example of a rigid and sturdy bottom anode that may be inserted into soil, while a top cathode may be in contact with the air. FIG. 9 includes a data meter (20), load (21), a cathode (27), a hollow tube separator (28), an anode (29) such as a brush, and perhaps even a spike (30). A spike (30) may be a bottom spike and may assist in inserting a device into a matrix.

Embodiments of the present invention may provide a load resistance in a system which may be any amount of resistance but may include, but is not limited to, between about 1 ohm to about 50000 ohms.

When an electrical signal may be measured (55), it may be correlated with a microbial activity of a matrix. For example, an electrical signal may be measured as a measured voltage. An amount of voltage may determine the microbial activity. This may include, but is not limited to, low microbial activity when said measured voltage is between about 0.1 to about 14 mV; moderate microbial activity when said measured voltage is between about 14.1 to about 25 mV; and high microbial activity when said measured voltage is greater than about 25 mV. A device may be inserted into a matrix for an amount of time such as but not limited to, about 5 minutes, greater than 5 minutes, and less than about 5 minutes.

In natural soil, low microbial activity may show that bioactivity may be low in soil, soil may not be healthy, or even that soil may be less productive if perhaps used for agricultural practice. Low microbial activity in soil may indicate, but is not limited to: 1) that the total microbial populations may be too low; 2) that key nutrients such as nitrogen, phosphorus and trace nutrients such as trace metals, or the like, may be limited; or perhaps even 3) that organic matter may be depleted or even at a low level that cannot support adequate microbial activities. In remediation applications, low microbial activity may show that remediation efforts may not be working or perhaps that remediation may be close to being or even complete. Low microbial activity in remediation applications may indicate, but is not limited to: 1) that total microbial populations or even capable microbial populations may be too low; 2) that key nutrients such as nitrogen, phosphorus and trace nutrients such as trace metals, or the like may be limited; 3) that in situ redox conditions such as redox potential and available electron acceptors, or the like, may not be proper for the indigenous microbes; 4) that in situ geochemical conditions such as pH, salinity, or the like may not be proper for indigenous microbes; or perhaps even 5) that a substrate including the target contaminant compound may be depleted or perhaps at low level that cannot support adequate microbial activities.

In natural soil, high microbial activity may show that bioactivity may be high in soil, that soil may be healthy, or even that soil may be more productive if used for agricultural practice. High microbial activity in soil may indicate, but is not limited to: 1) that total microbial populations may be high or even active; 2) that key nutrients such as nitrogen, phosphorus and trace nutrients such as trace metals, or the like, may be adequate, or perhaps even 3) that organic matter may be adequate. High microbial activity in remediation applications may indicate that the existing remediation efforts may be sound and perhaps even that operations may be maintained until the complete remediation may be achieved.

In natural soil, moderate microbial activity may show that bioactivity may be moderate in soil, that soil may be moderately healthy, or even that soil may be moderately productive if used for agricultural practice. Moderate microbial activity in soil may indicate, but is not limited to: 1) that total microbial populations may be moderate or moderately active; 2) that key nutrients such as nitrogen, phosphorus and trace nutrients such as trace metals, or the like may be adequate; or perhaps even 3) that organic matter content may be moderate. In remediation, moderate microbial activity may indicate that the existing remediation efforts may be sound. If contaminants may still be present at a high level, the operations may be improved perhaps to reach the high microbial activities. In remediation applications, moderate microbial activity may show that remediation efforts may not be working or perhaps that remediation may be on the track to complete, perhaps if confirmed by the decrease of contaminants. If contaminants remain at high level, moderate microbial activities may indicate a few possibilities, such as but not limited to: 1) that total microbial populations or capable microbial populations may be moderate and can be enhanced; 2) that key nutrients such as nitrogen, phosphorus and trace nutrients such as trace metals may be limited; 3) that in situ redox condition such as redox potential and available electron acceptors, or the like, may not be optimal for the indigenous microbes; 4) that in situ geochemical conditions such as pH, salinity, or the like may not be optimal for indigenous microbes. These deficiencies can be addressed and improved perhaps through engineering measures.

Laboratory and Field Studies

Laboratory Study 1: BioRemeter Monitoring Wastewater Treatment Performance

The maintenance of wastewater treatment performance may be determined by laboratory tests that may take hours to days to determine, which may result in delayed operations adjustments and repairs. One parameter that may determine wastewater treatment performance is chemical oxygen demand (COD), where a portable bioelectrochemical electrical signal measuring device can be a useful tool for real-time monitoring of COD. To demonstrate the applicability of a portable bioelectrochemical electrical signal measuring device for measuring COD levels in wastewater, laboratory tests were conducted to develop a correlation between measured voltage and COD.

Figure 10:
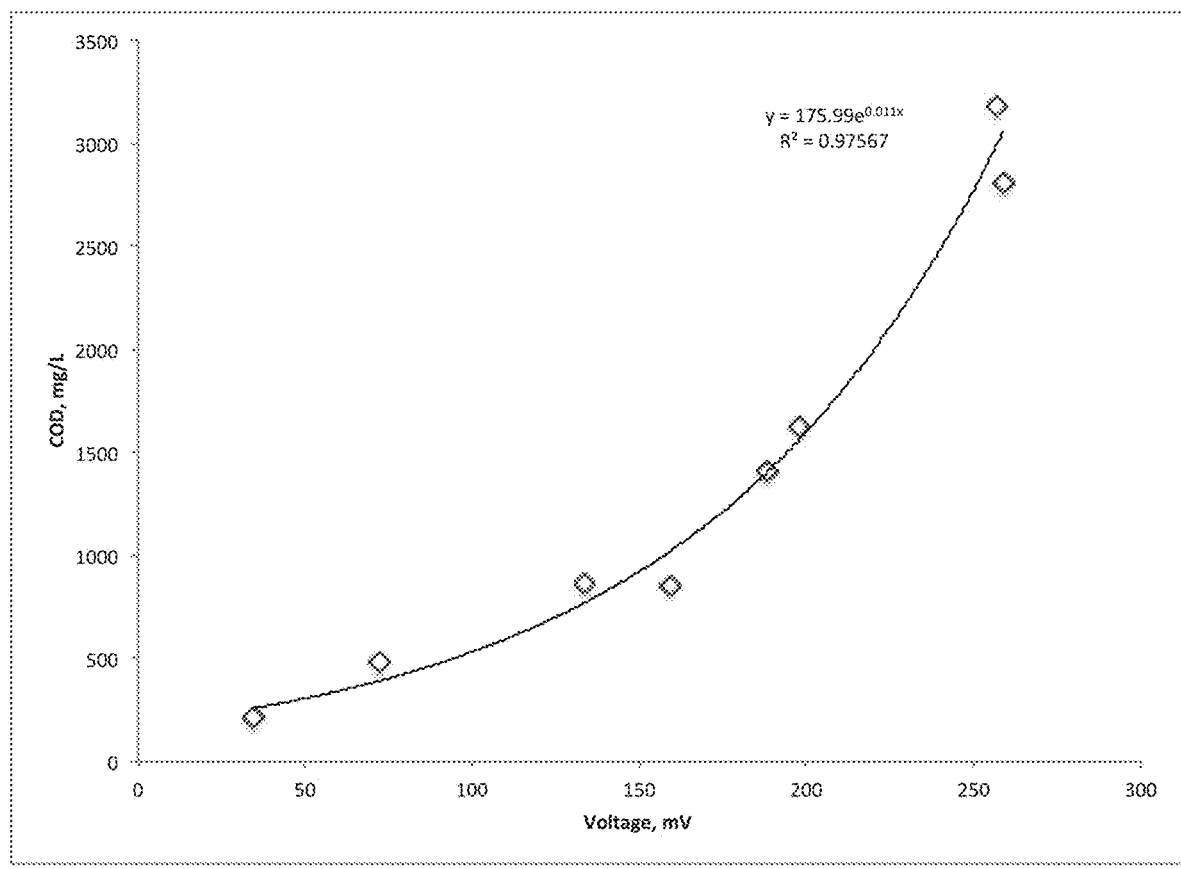
FIG. 10 shows a non-limiting example of a correlation between a measured voltage and chemical oxygen demand in wastewater in accordance with the various embodiments of the present invention.

Wastewater was collected from a local municipal wastewater treatment plant for the tests. The wastewater was added to open-batch reactors and were left to incubate at room temperature (about 20-23° C.). A device designed for wastewater applications was tested with a selected resistance level. The COD concentrations of the wastewater were monitored from samples collected at different times. Measurements were taken at the same time as the COD samples collection. FIG. 10 shows the correlation between the measured voltages and COD. The correlation was an exponential function of the measured voltage where the correlation coefficient was 0.976, perhaps indicating a high level of correlation between the voltage and COD concentrations.

Figure 11:
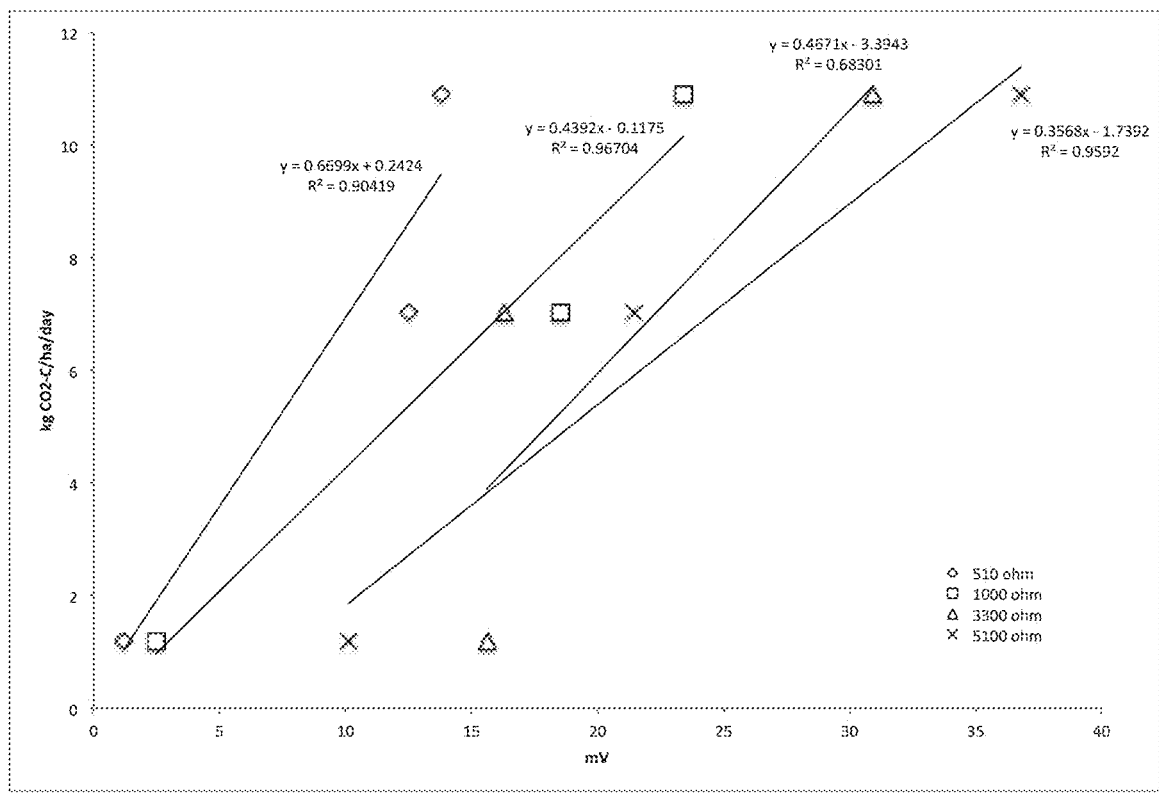
FIG. 11 shows a non-limiting example of a correlation of a measured voltage at different resistances and soil respiration in accordance with the various embodiments of the present invention.

Laboratory Study 2: Demonstration of Correlating BioRemeter Voltage with Soil Respiration Soil respiration may be a primary indicator of soil microbial activity and health. This parameter may typically be determined by measuring the amount of carbon dioxide produced for a certain amount of time. A laboratory study was conducted to correlate soil respiration with measured voltages at different resistances. Carbon dioxide and soil device measurements were conducted on a soil at different conditions that affect microbial activity. A portable bioelectrochemical electrical signal measuring device for soil was set at different resistances to establish an optimal load depending on microbial activity levels. As shown in FIG. 11, the soil respiration correlated well with measured voltages. A resistance of about 5100 ohms indicated an optimal load for measuring relatively higher microbial activities. Overall, this study indicated that the a portable bioelectrochemical electrical signal measuring device for soil may be a viable alternative to measuring carbon dioxide that involves using expensive disposable measuring supplies.

Field Study 1: In Situ Determination of Groundwater Microbial Activity at a Bioremediation Project Site BioRemeter An experiment demonstrated the use of a portable bioelectrochemical electrical signal measuring device at a former petroleum bulk plant facility with groundwater contaminant plume consisting of petroleum hydrocarbons. A bioremediation treatment was injected into groundwater wells at this site to enhance microbial biodegradation activity. To determine the effectiveness and dispersion of the treatments, a portable bioelectrochemical electrical signal measuring device designed for groundwater applications was tested to detect the level of microbial activity.

The a portable bioelectrochemical electrical signal measuring device demonstration was conducted at the following groundwater wells:

MW-A [Considered to be an un-impacted background well down-gradient from the plume and treatment area]
MW-B [Up-gradient from MW-A, and down-gradient near the treatment area]
MW-C [within the treatment area, down-gradient from a treatment well OW-D, and used for performance monitoring]
OW-D [Treatment well]
OW-E [Treatment well containing a treatment sock, and where nutrient injections have been conducted]

The measured voltage readings are shown in the Table 1 below:

TABLE 1

| Well ID | Voltage, mV |
|---|---|
| MW-A | 6.0 |
| MW-B | 7.3 |
| MW-C | 9.1 |
| OW-D | 9.3 |
| OW-E | 10.6 |

The lowest microbial activity level correlated with the lowest voltage, which was at the un-impacted well MW-A. Higher microbial activity levels correlated with higher voltages, where voltages increased near and at the treatment wells. Overall, the field test indicated that the effectiveness of the treatment decreased with increasing distance from the treatment wells.

Figure 12:
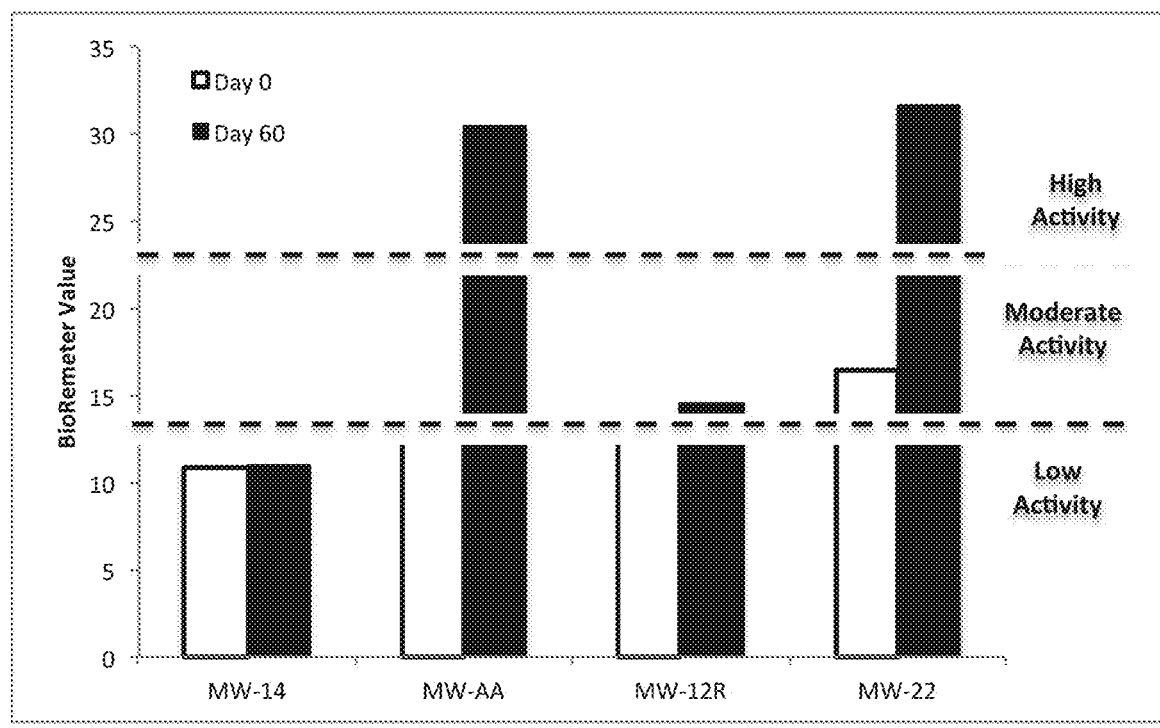
FIG. 12 shows microbial activities in groundwater wells in accordance with the various embodiments of the present invention.
Figure 13:
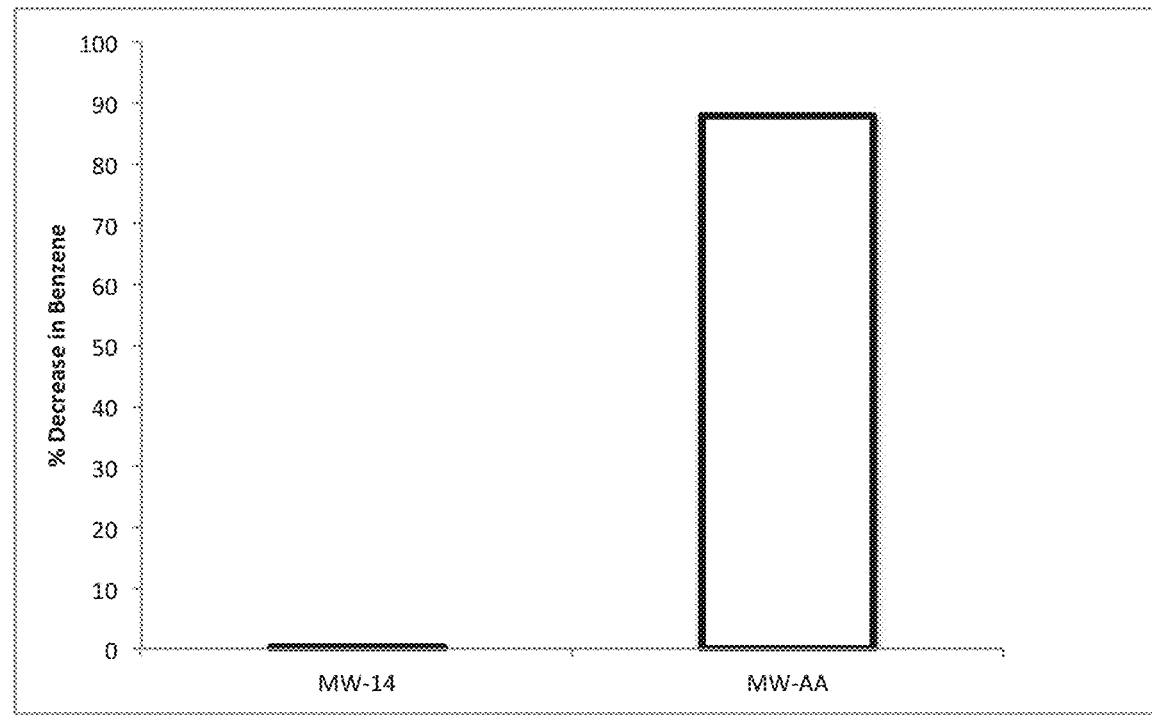
FIG. 13 shows an example of a percentage decreases in benzene concentrations in groundwater wells in accordance with the various embodiments of the present invention.

Field Study 2: In Situ Determination of Treatment Effectiveness on Microbial Activity Enhancement by BioRemeter Laboratory and field tests of a portable bioelectrochemical electrical signal measuring device may have resulted in the establishment of voltage ranges that correlate with microbial activity levels. Low activity may correlate with a voltage range of about 1.0—about 14.0 mV. Moderate activity may correlate with a voltage range of about 14.1—about 23.0 mV. High activity may correlate with voltages>about 23.1 mV. A microbial enhancement treatment was implemented at a fuel station with benzene-contaminated groundwater. To demonstrate that the treatment was increasing microbial activity in the groundwater, portable bioelectrochemical electrical signal measuring device surveys of the site were conducted before the treatment implementation and about 60 days after the treatment implementation. Selected wells used for monitoring the microbial activity changes were MW-14, MW-AA, MW-12R, and MW-22. Wells MW-14 was outside the treatment area, while the other three wells were within the treatment area. As shown in FIG. 12, microbial activities increased in wells within the treatment area, but little change in microbial activity was observed outside the treatment area (indicated by MW-14). The level of benzene biodegradation was very low for MW-14 and higher for MW-AA (FIG. 13), perhaps confirming the interpretation of the measurements. Overall, this study seems to have demonstrated that a portable bioelectrochemical electrical signal measuring device may be an effective in situ (or ex situ) BEC tool such as to determine the effectiveness of bioremediation treatments by measuring relative microbial activities via voltage drop.

As can be easily understood from the foregoing, the basic concepts of the present invention may be embodied in a variety of ways. It involves both measurement techniques as well as devices to accomplish the appropriate measurement. In this application, the measurement techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible: many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of an "insert" should be understood to encompass disclosure of the act of "inserting"—whether explicitly discussed or not—and, conversely, were there effectively disclosure of the act of "inserting," such a disclosure should be understood to encompass disclosure of an "insert" and even a "means for inserting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the attached information disclosure statement or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the measurement devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such processes, methods, systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC*, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method of measuring microbial activity comprising the steps of:
    providing a portable bioelectrochemical electrical signal measuring device comprising:
        at least one anode located together with at least one cathode, wherein said at least one cathode and said at least one anode are separated by and attached to a permeable material or wherein said at least one cathode and said at least one anode are enclosed in a permeable casing;
        an anode-cathode connector between said at least one anode and said at least one cathode;
        a load connector between a load and said at least one anode and at least one cathode; and
        a data meter connected to said load connector;
    providing a natural remediation matrix containing microorganisms or biological enzymes;
    inserting said portable bioelectrochemical electrical signal measuring device into said natural remediation matrix containing microorganisms or biological enzymes;
    measuring an electrical signal of said natural remediation matrix with said portable bioelectrochemical electrical signal measuring device;
    removing said portable bioelectrochemical electrical signal measuring device from said natural remediation matrix; and
    determining microbial activity in said natural remediation matrix based on said measured electrical signal.

2. The method of measuring microbial activity as described in claim 1 wherein said natural remediation matrix comprises soil and wherein said step of determining said microbial activity comprises real-time monitoring of carbon dioxide of said soil.

3. The method of measuring microbial activity as described in claim 1 wherein said natural remediation matrix comprises a contaminated groundwater and wherein said step of determining said microbial activity comprises real-time monitoring of a voltage of said contaminated groundwater.

4. The method of measuring microbial activity as described in claim 1 wherein said data meter is selected from a group consisting of multimeter, voltmeter, and electrical data logger.

5. The method of measuring microbial activity as described in claim 1 wherein said step of providing said natural remediation matrix containing microorganisms or biological enzymes comprises a step of providing a natural remediation matrix with at least one originally contained organic compound or contaminant.

6. The method of measuring microbial activity as described in claim 1 and further comprising a step of providing a load resistance of between about 1 ohm to about 50000 ohms.

7. The method of measuring microbial activity as described in claim 1 wherein said at least one cathode and said at least one anode are separated by and attached to said permeable material and further comprising providing a hollow tube in said portable bioelectrochemical electrical signal measuring device.

8. The method of measuring microbial activity as described in claim 7 wherein said hollow tube comprises a perforated tube.

9. The method of measuring microbial activity as described in claim 8 wherein said perforated tube is filled with an element chosen from air, a solid, a liquid, dissolved oxygen, oxygen releasing compounds, and any combination thereof.

10. The method of measuring microbial activity as described in claim 8 wherein said perforated tube is filled with oxygen releasing compounds chosen from magnesium peroxide, calcium peroxide, hydrogen peroxide, percarbonate, ozone, organic peroxides, permanganate, persulfate, and ferrate.

11. The method of measuring microbial activity as described in claim 1 and further comprising a spike on said portable bioelectrochemical electrical signal measuring device.

12. The method of measuring microbial activity as described in claim 1 wherein said step of measuring said electrical signal of said natural remediation matrix comprises a step of measuring a voltage or amperage of said natural remediation matrix.

13. The method of measuring microbial activity as described in claim 1 and further comprising a step of correlating said measured electrical signal of said natural remediation matrix with a microbial activity in said natural remediation matrix.

14. The method of measuring microbial activity as described in claim 13 wherein said correlation is selected from a group consisting of:
    low microbial activity when said measured voltage is between about 0.1 to about 14 mV; moderate microbial activity when said measured voltage is between about 14.1 to about 25 mV; and high microbial activity when said measured voltage is greater than about 25 mV.

15. The method of measuring microbial activity as described in claim 1 wherein at least part of said at least one cathode is coated with a permeable, waterproof material.

16. The method of measuring microbial activity as described in claim 1 wherein said natural remediation matrix is chosen from soil, groundwater, sediment, surface water, wastewater, energy process matrix, and a liquid phase in biogas process.

17. The method of measuring microbial activity as described in claim 1 wherein said natural remediation matrix contains said microorganisms, wherein said microorganisms are chosen from indigenous microorganisms, commercially available microorganisms, microorganisms that are capable of degrading the contained electron-donating compounds, facultative bacteria, iron-reducing bacteria, sulfate-reducing bacteria, metal-reducing bacteria, denitrifying bacteria, methane-producing bacteria, archaea, dechlorinating bacteria, and fermentative bacteria.

18. The method of measuring microbial activity as described in claim 1 wherein said step of measuring said electrical signal of said natural remediation matrix with said portable bioelectrochemical electrical signal measuring device comprises the step of measuring said electrical signal for a matrix measurement time chosen from about 5 minutes, greater than 5 minutes, and less than about 5 minutes.

19. A microbial activity measurement system comprising:
  a portative, transitory bioelectrochemical insert capable of measuring electrical signals originated from microbial metabolisms in a natural remediation matrix containing microorganisms or biological enzymes;
  wherein said portative, transitory bioelectrochemical insert comprises:
    at least one anode located together with at least one cathode, wherein said at least one cathode and said at least one anode are separated by and attached to a permeable material or wherein said at least one cathode and said at least one anode are enclosed in a permeable casing;
    an anode-cathode connector between said at least one anode and said at least one cathode;
    a load connector between a load and said at least one anode and said at least one cathode; and
    a data meter connectable to said load connector.

20. The microbial activity measurement system as described in claim 19 wherein said natural remediation matrix comprises a matrix with at least one originally contained organic compound or contaminant.

21. The microbial activity measurement system as described in claim 19 wherein said measured electrical signals of said natural remediation matrix correlates to microbial activity in said natural remediation matrix.

22. The microbial activity measurement system as described in claim 21 wherein said correlation is selected from a group consisting of:
  low microbial activity when said measured voltage is between about 0.1 to about 14 mV; moderate microbial activity when said measured voltage is between about 14.1 to about 25 mV; and
  high microbial activity when said measured voltage is greater than about 25 mV.

* * * * *